United States Patent

Morrow, III

[11] Patent Number: 5,792,665
[45] Date of Patent: Aug. 11, 1998

[54] OXYGEN SENSING METHOD AND HAND HELD ANALYZER THEREFORE

[76] Inventor: Donald W. Morrow, III, 1840 Bracken Rd., Richmond, Va. 23236

[21] Appl. No.: 655,059

[22] Filed: May 29, 1996

[51] Int. Cl.$^6$ .......................... G01N 29/18; G01N 29/02
[52] U.S. Cl. .......................... 436/136; 73/24.01; 73/24.02
[58] Field of Search .......................... 436/136; 73/24.01, 73/24.02; 128/660.02

[56] References Cited

U.S. PATENT DOCUMENTS

| | | | |
|---|---|---|---|
| 3,276,241 | 10/1966 | Hubner | 73/23 |
| 4,280,183 | 7/1981 | Santi | 364/497 |
| 4,520,654 | 6/1985 | Terhune | 73/24 |
| 4,562,723 | 1/1986 | Hubner | 73/23 |
| 4,879,546 | 11/1989 | Dunham et al. | 73/24 |
| 5,060,506 | 10/1991 | Douglas | 73/24.01 |
| 5,285,677 | 2/1994 | Oehler | 73/24.01 |
| 5,351,522 | 10/1994 | Lura | 73/24.01 |
| 5,419,326 | 5/1995 | Harnoncourt | 128/660.02 |
| 5,503,155 | 4/1996 | Harnoncourt et al. | 128/660.02 |

FOREIGN PATENT DOCUMENTS

| | | |
|---|---|---|
| 55-87037 | 7/1980 | Japan . |
| 9203724 | 3/1992 | WIPO . |

OTHER PUBLICATIONS

W. R. Dagle *Chem. Abstr.* 1989, 110, 169486p.
Oxyalert™ Mk 8–D Evaluation Guide, Sep. 1994, Douglas Scientific Inc., Lenexa, Kansas.

*Primary Examiner*—Arlen Soderquist
*Attorney, Agent, or Firm*—Shoemaker & Mattare, Ltd.

[57] ABSTRACT

An oxygen analyzer is provided to detect the oxygen concentration of both a control gas and the output of an oxygen concentrator using ultrasound technology. The analyzer uses a calibration mode to alter the analyzer's output when calibrating it on the control gas. The analyzer is then switched back to its normal mode to permit a therapist to check the percentage of oxygen in the gas being supplied by an oxygen concentrator.

14 Claims, 2 Drawing Sheets

OXYGEN SENSING METHOD AND HAND HELD ANALYZER THEREFORE

FIELD OF THE INVENTION

The present invention is directed to a method of sensing oxygen and a hand held oxygen analyzer and, in particular, to a hand held oxygen analyzer which can be used on both bottled pure oxygen and oxygen supplied by an oxygen concentrator.

BACKGROUND ART

Oxygen concentrators to supply supplemental oxygen in the therapeutic treatment of respiratory and pulmonary disorders are often used in a patient's home. These concentrators pull in the surrounding room air and, through a filtering process, removes the nitrogen from the air. The nitrogen is trapped in a molecular sieve material so that the concentrator can deliver a gas to the patient having approximately 95% oxygen.

The output of these concentrators must be periodically checked to assure that the level of oxygen in the output gas is sufficiently high. This checking is often done by a respiratory therapist which make periodic visits to the homecare patients. These therapist check the output of the oxygen concentrator to assure that the patient is receiving about 95% pure oxygen. If the oxygen concentration drops below 90%, the concentrator must be replaced or repaired.

During these homecare patient visits, the therapist uses a hand held analyzer to check the oxygen purity of the concentrator. The present day hand held analyzer uses a fuel cell to measure oxygen purity. Fuel cells are like a battery in that, when oxygen passes through them, the fuel cells give off a charge. The amount of charge emitted is directly related to the purity of the passing oxygen, the purer the oxygen, the greater the charge and vice-a-versa.

When a therapist is checking the output of the oxygen concentrator, the therapist must first calibrate the hand held analyzer. Normally, this is done through the use of a small tank of medical grade oxygen. The hand held analyzer is used to measure the oxygen purity of the medical grade oxygen provided in the tank, i.e., detect 100% oxygen. Knowing that the hand held analyzer is properly calibrated, the therapist can then use the hand held analyzer to make sure that the oxygen concentrator is providing the necessary percent oxygen in the gas being supplied to the patient.

Prior art hand held analyzers relying on fuel cell technology for oxygen concentration measurement are not without their disadvantages. The use of the fuel cell requires frequent calibration of the unit. Moreover, the purer the oxygen or the greater the volume or flow of oxygen passing across the fuel cell, the greater the drain of cell power. Typically, a fuel cell lasts only approximately one year and costs about $75.00 to replace. The fuel cells are also adversely effected by barometric pressure and temperature.

In view of the disadvantages noted above with respect to hand held analyzers using fuel cells for checking the output of oxygen concentrators, a need has developed to provide a more reliable and cost efficient alternative. Responsive to this need, the present invention provides a method of oxygen analyzing and a hand held analyzer which uses ultrasound technology to provide a more accurate and responsive analyzer.

The use of sound waves to measure oxygen concentration in a gas is known. For example, Douglas Scientific, Inc. of Lenexa, Kans. manufactures an OxyAlert™ Mk 8-D instrument which functions as an oxygen concentrator monitor. The instrument is described in an evaluation guide published September, 1994, and herein incorporated in its entirety by reference. The instrument is designed to be attached to or made part of an oxygen concentrator. The instrument also includes warning lights and an audio alarm and/or visual alarm signal to warn a patient or caretaker of a drop in oxygen concentration in the gas produced by the oxygen concentrator.

Since the OxyAlert™ instrument is made part of the concentrator, it cannot function as a hand held analyzer. The OxyAlert™ also is incapable of being field calibrated using medical grade oxygen.

SUMMARY OF THE INVENTION

It is a first object of the present invention to provide an improved hand held analyzer for monitoring the output of an oxygen concentrator.

Another object of the present invention is to provide a hand held oxygen analyzer which is not sensitive to barometric pressure, temperature or the rate of flow or pressure of gas being supplied by an oxygen concentration.

A further object of the present invention is to provide a hand held oxygen analyzer which provides quick response, is highly accurate and is low in cost.

It is a still further object of the present invention to provide a method for checking the output of an oxygen concentrator in a reliable and easy to use fashion.

Other objects and advantages of the present invention will become apparent as a description thereof proceeds.

In satisfaction of the foregoing objects and advantages, the present invention provides a hand held oxygen analyzer which comprises a housing having a gas inlet and a means for sensing the concentration of oxygen in an argon-containing gas using sound waves, the sensing means in communication with the gas inlet. The sensing means produces a signal indicative of the concentration of oxygen in the gas. Also provided is a means for adjusting the signal to account for a lack of argon in a gas supplied to the gas inlet for calibration purposes. The hand held oxygen analyzer also includes a means for displaying an oxygen concentration based on the signal produced when sensing a gas containing argon and the adjusted signal.

The hand held analyzer is preferably powered by a battery and includes a switch displaying either the oxygen concentration based on the sensed signal or the adjusted signal.

In the inventive method, oxygen output from an oxygen concentrator is sensed by first providing a hand held oxygen analyzer which can sense oxygen concentration of a gas containing argon using sound waves. The analyzer is put in a calibrate mode and a supply of pure oxygen gas is provided to the hand held oxygen analyzer and the output of the oxygen analyzer is adjusted to account for a lack of argon in the pure oxygen supplied gas. The adjusted output is then displayed.

After the oxygen analyzer is adjusted or calibrated, it is put in a normal mode. A supply of gas having a high percentage of oxygen is then supplied to the hand held oxygen analyzer. The analyzer senses the concentration of oxygen in the supply gas and displays its concentration. Preferably, the high percentage oxygen gas is at least 90% oxygen when supplied to the analyzer. The concentration is preferably displayed in a percentage and the analyzer is supplied with battery power. Preferably, the pure oxygen gas is supplied in pressurized form from a container.

DESCRIPTION OF THE PREFERRED EMBODIMENTS

The inventive oxygen analyzer is a portable battery powered type having the capability of being calibrated against a control in field use. The inventive oxygen analyzer is more reliable than prior art devices and is not adversely effected by environmental or other external factors. Since the oxygen analyzer uses ultrasound technology, the need for a fuel cell is eliminated as well as the disadvantages associated therewith. The inventive analyzer is more accurate than fuel cell-containing analyzers. Fuel cell analyzers are generally only accurate to within 2% while the inventive oxygen analyzer has an accuracy within plus or minus 0.5%.

Figure 1:
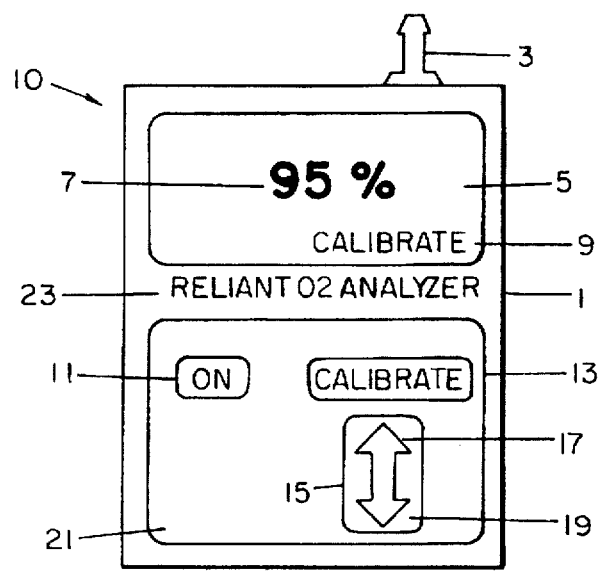
FIG. 1 shows the oxygen analyzer.

Referring now to FIG. 1, the inventive oxygen analyzer is generally designated by the reference numeral 10 and is seen to include a housing having a gas inlet 3 extending therefrom. The gas inlet 3 is designed to receive tubing or the like so that the analyzer 10 can be connected to a source of an oxygen-containing gas such as medical grade bottled oxygen or the oxygen supplied by an oxygen concentrator.

The analyzer also includes a LCD display 5 which indicates the oxygen concentration in terms of a percentage display 7. The LCD display also displays the term "calibrate" designated by reference numeral 9 to indicate when the analyzer is in the calibrate mode.

The housing also includes a touch pad-type on/off button 11, a touch pad-type calibrate button 13 and a touch pad-type calibration adjustment button 15 with both an up button 17 and a down button 19. The touch pad-type buttons are covered by the key pad 21. The housing may also include indicia 23 to identify a tradename or the like.

The method of using the oxygen analyzer will now be described. As discussed above, when homecare patients are given oxygen therapy, they are supplied with an oxygen concentrator at their home. At periodic intervals, a respiratory therapist will visit the homecare patient and make sure that the oxygen concentrator is supplying the required level of oxygen in the gas emitting therefrom. The respiratory therapist is supplied with both the inventive analyzer and a small tank of medical grade oxygen for analyzer calibration.

Prior to checking the oxygen concentrator with the analyzer, the therapist must first calibrate the analyzer using the tank of medical grade oxygen (not shown). First, the therapist presses the on button 11 and then the calibrate button 13 to display the term "calibrate" 9 in the display 5. The calibrate mode allows the analyzer to compensate for the absence of argon in the control gas since the analyzer is designed to account for the argon in the gas supplied by the oxygen concentrator. The medical grade oxygen tank is then hooked up to the gas inlet 3 and the therapist reads the display 7. If the display reads 100%, no adjustment using the adjustment buttons 17 and 19 is needed. If the display reads other than 100%, the up or down buttons, 17 and 19, respectively, are pushed so that the read out of the display is 100%.

The calibrate button 13 is then depressed to place the oxygen analyzer in its normal position and the gas inlet is then attached to the output port of the concentrator to read, sense and display the oxygen concentration of the gas emanating from the concentrator output. Typically, this percentage should read about 95%. In certain instances, as low as 90% oxygen is acceptable for oxygen therapy.

If desired, the calibrate term 9 can be designed to flash when in the calibrate mode. The up and down buttons 7 are preferably membrane switches which is used to adjust the zero potentiometer of the analyzer down in resistance. The calibration adjust down button is also a membrane switch used to adjust the zero potentiometer up in resistance.

The housing 1 is preferably made of plastic to house to circuit board of the analyzer, the transducer thereof and the battery (not shown) as the analyzer power source. The analyzer can be powered by alternating current or any other known power source.

Figure 2:
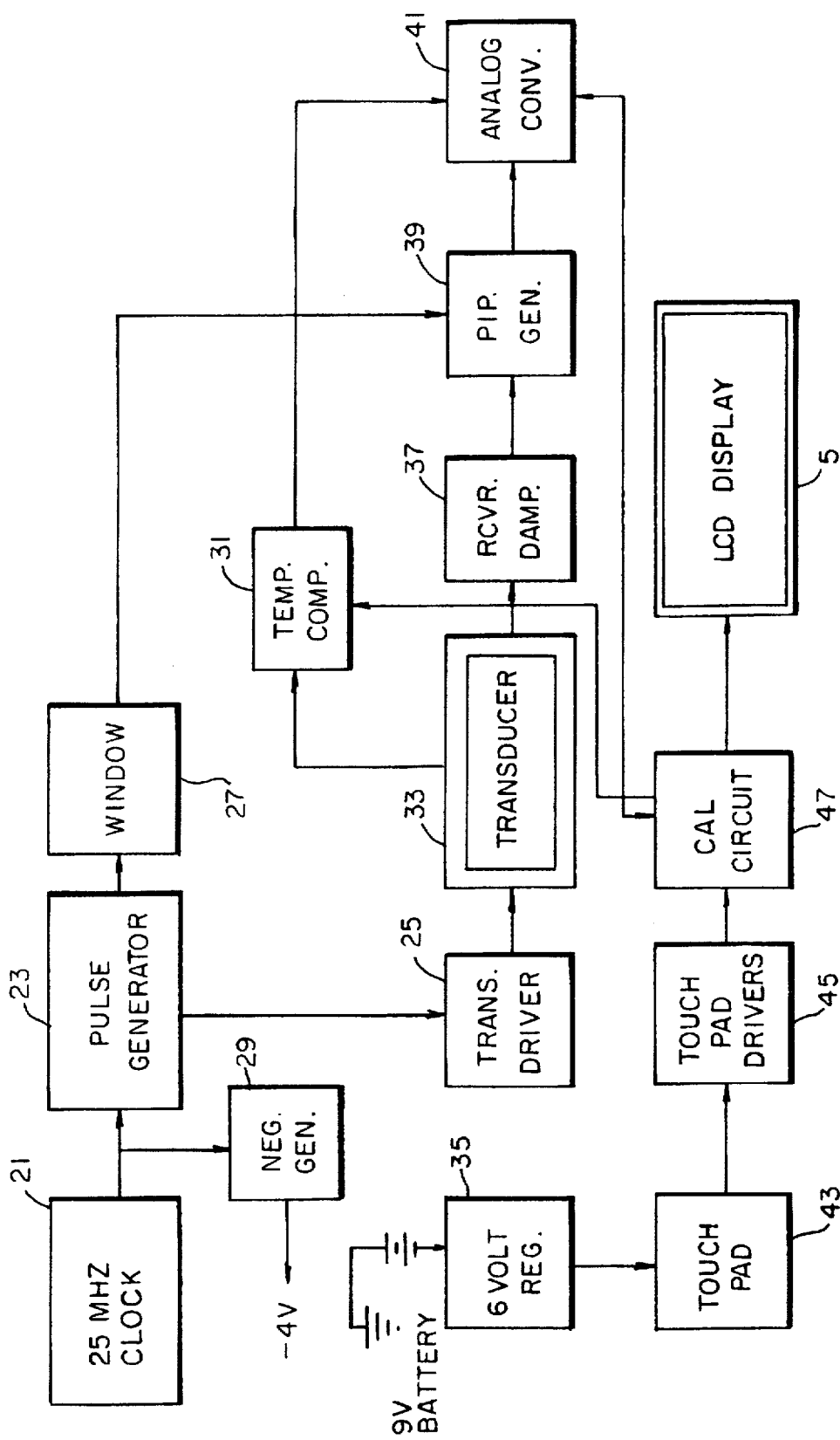
FIG. 2 is a schematic block diagram showing the function of the analyzer.

With reference now to FIG. 2, a schematic block diagram is illustrated showing the function of the oxygen analyzer. First, a 25 MHz clock sets up the timing function for the system logic of the analyzer. Through the system logic, a pulse generator 23 produces three pulses that drive the transmitter circuit 25 and control the window circuit 27. The window circuit 27 opens to capture a voltage produced by the first harmonic of the sound wave for use in calculating the percent of oxygen.

A negative generator circuit 29 is used to produce a minus 4 volts on its output as a reference for the integrated circuits.

A temperature compensation circuit 31 is provided to take into account the temperature of the gases in the transducer 33 and account for any temperature variation.

A 5 volt regulator circuit 35 is provided which takes a 9 volt supply from the battery and regulates the output to 5 volts to power the device.

The transducer 33 consists of a chamber in which gases pass through an ultrasonic wave which measures the molecular weight of the gas detected. The signal then enters a receiver 37 which decodes and dampens the signal due to the responsiveness of the transducer to fluctuations in the oxygen output of the gas being sensed. From the receiver 37, a pip generator 39 triggers a sample and hold circuit to obtain the proper ramp voltage which is selected for the analog output. Once selected, the signal is converted and the temperature effects are cancelled through an analog converter 41.

The touch pad 43 is a set of membrane switches that, when depressed, control the on/off operation of the analyzer and the calibration of the unit. The touch pad driver 45 has the logic circuits that perform the functions once a switch is depressed. The calibration circuit 47 is needed to complete the output of the circuit and display it in the calibration mode. The LCD display 5 shows in digital numerical format the output and percent of oxygen that is determined by the circuit.

It should be understood that, except for the touch pad 43, touch pad drivers 45 and calibration circuit 47, the components illustrated in FIG. 2 are part of the Douglas Scientific OxyAlert™ analyzer discussed above. The alarms, LED and delay circuits associated with the OxyAlert™ analyzer are removed since they draw excess of power and are not needed for the inventive analyzer.

Figure 3:
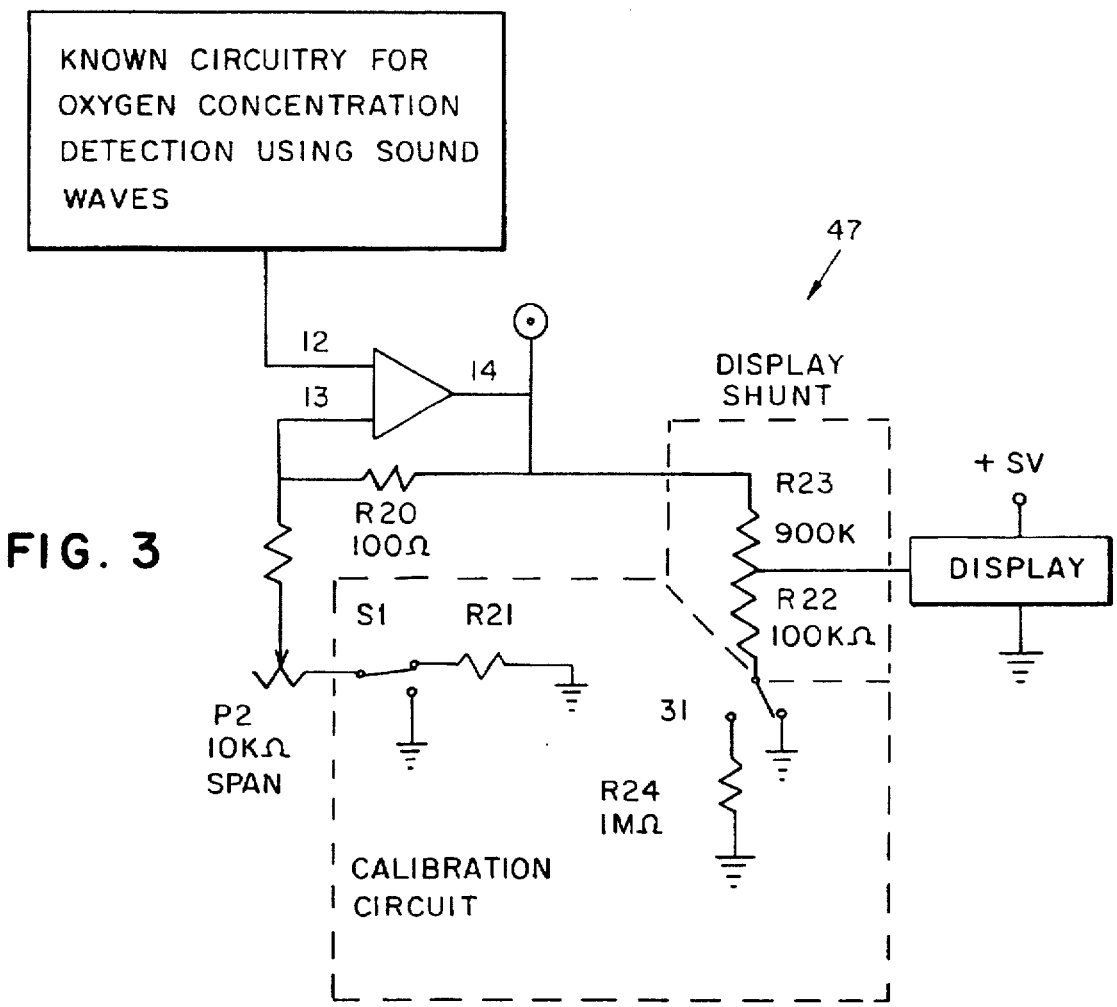
FIG. 3 shows the calibration circuit.

Referring now to FIG. 3, the calibration circuit 47 is shown in more detail in conjunction with the known circuitry for the oxygen concentration detection using sound waves. The calibration circuit 47 is outlined in the cross hatching and comprises R21 which is switched to ground in the calibration mode to manipulate the output of the known circuitry to read 0.897 volts for pure oxygen. R22 and R23 make up the transistor network that allows the 200 millivolt display to accept up to 2 volts input voltage. R24 is the resistor that is switched in during calibration for making the display read 1 volt for 100% oxygen when the known circuitry output is 0.897 volts. In other words, the known circuitry for oxygen concentration detection would output a signal of 0.897 volts for pure oxygen since the known circuitry accounts for argon which is not present in the medical grade control oxygen gas. Consequently, the calibration circuit 47 alters the output of the known circuitry from 0.897 volts for pure oxygen to read 1 volt or 100% oxygen for display purposes. Thus, when the inventive oxygen analyzer is put in the calibration mode it can sense pure oxygen using the known circuitry and provide a correct reading of 100% oxygen. The calibration circuit can then be disengaged so that the analyzer when reading the output of an oxygen concentrator which derives in its oxygen from room air that contains argon will give the correct oxygen percentage.

As such, an invention has been disclosed in terms of preferred embodiments thereof which fulfill each and every one of the objects of the present invention as set forth hereinabove and provides a new and improved oxygen analyzer and method for sensing oxygen concentration in a gas.

Of course, various changes, modifications and alterations from the teachings of the present invention may be contemplated by those skilled in the art without departing from the intended spirit or scope thereof. Accordingly, it is intended that the present invention only be limited by the terms of the appended claims.

I claim:

1. A hand held oxygen analyzer comprising:

a) a housing having a gas inlet;

b) a means for sensing a concentration of oxygen in a gas containing argon using sound waves and producing a signal indicative of said concentration; said sensing means in communication with said gas inlet;

c) a means for adjusting said signal to account for a lack of argon in an substantially pure oxygen gas when supplied to said inlet in a calibration mode;

d) means for calibrating the analyzer when said substantially pure oxygen gas is supplied during the calibration mode to read 100% when it does not already read that level as a result of the adjusting means; and e) means for displaying an oxygen concentration based on one of said signal and said adjusted signal.

2. The analyzer of claim 1, wherein said housing includes a switch to display the oxygen concentration based on one of the signal and the adjusted signal.

3. The analyzer of claim 1, further comprising a power source for supplying power to said sensing means, adjusting means and display means.

4. The analyzer of claim 3, further comprising means for providing 5 volt power from said power source.

5. The analyzer of claim 3, wherein said power source is a battery.

6. A method of sensing oxygen output from an oxygen concentrator comprising the steps of:

a) providing a hand held oxygen analyzer which senses oxygen concentration of a gas containing argon using sound waves;

b) providing a supply of pure oxygen gas to said hand held oxygen analyzer;

c) adjusting an output of said oxygen analyzer to account for a lack of argon in said supply of pure oxygen gas, displaying said adjusted output, and calibrating said analyzer;

d) providing a supply of argon containing gas from said oxygen concentrator; and e) sensing the concentration of oxygen in said supply of gas and displaying said sensed concentration.

7. The method of claim 6, wherein the oxygen concentration in said supply of gas is at least 90% oxygen.

8. The method of claim 6, wherein the concentration of oxygen are displayed in percentages.

9. The method of claim 6, wherein said hand held oxygen analyzer is supplied with battery power.

10. The method of claim 6, wherein said supply of pure oxygen gas is provided by a container having said pure oxygen gas in pressurized form.

11. A hand held oxygen analyzer comprising:

a) a housing having a display, gas inlet, an on-off switch, a calibration on-off switch and a pair of calibration adjustment switches;

b) a means operable by actuation of the calibration on-off switch to the off position for sensing the concentration of oxygen in a gas containing argon using sound waves and producing a signal indicative of said concentration; said sensing means in communication with said gas inlet and means for displaying said signal as a percent oxygen on said display;

c) means operable by actuation of the calibration on-off switch to the on position for adjusting the signal to account for a lack of argon in a gas supplied to said gas inlet and means for displaying said adjusted signal as a percent oxygen on said display; and d) a power source for said sensing means, said display means and said adjusting means.

12. The analyzer of claim 11, wherein said display is a liquid crystal display.

13. The analyzer of claim 11, wherein said power source is a battery.

14. The analyzer of claim 13, wherein an output of said battery is controlled to 5 volts.

* * * * *